United States Patent
Crockatt et al.

(10) Patent No.: US 11,932,616 B2
(45) Date of Patent: Mar. 19, 2024

(54) DIELS-ALDER RING-OPENING PROCESS

(71) Applicant: Nederlandse Organisatie voor toegepast-natuurwetenschappelijk onderzoek TNO, 's-Gravenhage (NL)

(72) Inventors: Marc Crockatt, 's-Hertogenbosch (NL); Johan Urbanus, 's-Gravenhage (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 344 days.

(21) Appl. No.: 17/047,573

(22) PCT Filed: Apr. 30, 2019

(86) PCT No.: PCT/NL2019/050250
§ 371 (c)(1),
(2) Date: Oct. 14, 2020

(87) PCT Pub. No.: WO2019/212338
PCT Pub. Date: Nov. 7, 2019

(65) Prior Publication Data
US 2021/0115005 A1    Apr. 22, 2021

(30) Foreign Application Priority Data

Apr. 30, 2018 (EP) .................................... 18170098

(51) Int. Cl.
| C07D 307/89 | (2006.01) |
| C07C 51/087 | (2006.01) |
| C07C 67/30 | (2006.01) |
| C07C 253/30 | (2006.01) |
| C07D 209/48 | (2006.01) |
| C07D 307/88 | (2006.01) |

(52) U.S. Cl.
CPC .......... *C07D 307/89* (2013.01); *C07C 51/087* (2013.01); *C07C 67/30* (2013.01); *C07C 253/30* (2013.01); *C07D 209/48* (2013.01); *C07D 307/88* (2013.01)

(58) Field of Classification Search
CPC .. C07D 307/89; C07D 209/48; C07D 307/88; C07C 51/087; C07C 67/30; C07C 253/30
See application file for complete search history.

(56) References Cited

U.S. PATENT DOCUMENTS 7,658,937 B2    2/2010    Nair et al.

FOREIGN PATENT DOCUMENTS

| JP | 2016193897 A | 11/2016 |
| WO | 2005113478 A2 | 12/2005 |
| WO | 2008128618 A1 | 10/2008 |
| WO | 2010012442 A2 | 2/2010 |
| WO | 2016099274 A1 | 6/2016 |
| WO | WO-2016099274 A1 * | 6/2016 ............ C07C 51/31 |
| WO | 2017004349 A2 | 1/2017 |

OTHER PUBLICATIONS

Thiyagarajan, Shanmugam, et al. "A Facile Solid-Phase Route to Renewable Aromatic Chemicals from Biobased Furanics." Angewandte Chemie 128.4 (2016): 1368-1371.

Lin, Zhaojia, et al., "Phthalic Anhydride Production from Hemicellulose Solutions: Technoeconomic Analysis and Life Cycle Assessment." AIChE Journal 61.11 (2015): 3708-3718.

Kotha, Sambasivarao et al., "Enantioselective Synthesis of (+)-4-Demethoxy-1, 4-Dimethyldaunomycinone." Bioorganic & Medicinal Chemistry 10.3 (2002): 621-624.

Kirchwehm, Yvonne, et al. "Ortho-Methylated Tribenzotriquinacenes—Paving the Way to Curved Carbon Networks." Chemical Communications 48.10 (2012): 1502-1504.

Hennige, Hans, et al. "Untersuchungen zur Chemie von Isoindolen und Isoindoleninen, XXVIII. 3-Alkoxy-1H-isoindole—Synthesen und Eigenschaften." Chemische Berichte 121.2 (1988): 243-252.

Shiramizu, Mika, et al., "On the Diels-Alder Approach to Solely Biomass-Derived Polyethylene Terephthalate (PET): Conversion of 2, 5-Dimethylfuran and Acrolein into P-Xylene." Chemistry—A European Journal 17.44 (2011): 12452-12457.

Thiyagarajan, Shanmugam, et al. "Substituted Phthalic Anhydrides from Biobased Furanics: A New Approach to Renewable Aromatics." ChemSusChem 8.18 (2015): 3052-3056.

Ghosh, Ketaki, et al., et al., "Total Synthesis of Neo-Tanshinlactones through a Cascade Benzannulation-Lactonization as the Key Step." European Journal of Organic Chemistry 2013.19 (2013): 4037-4046.

Dhananjeyan, Mugunthu R., et al. "Synthesis and Activity of Substituted Anthraquinones Against a Human Filarial Parasite, Brugia M Alayi." Journal of Medicinal Chemistry 48.8 (2005): 2822-2830.

Newman, Melvin S., et al., "Improved Synthesis of 3-Methylphthalic Anhydride." The Journal of Organic Chemistry 42.8 (1977): 1478-1479.

Nasman, J-AH. "A Versatile Synthetic Route to 3-Hydroxyphthalic Anhydride." Synthesis (Stuttgart) 8 (1985): 788-789.

Chan, Tze-Lock, et al. "A Stable Derivative of Cyclooctatrienyne: Synthesis and Crystal Structures of 1, 4, 7, 10-Tetramethyl-5, 6-Didehydrodibenzo [a, e] Cyclooctene and 1, 4, 7, 10-Tetramethyldibenzo [a, e] Cyclooctene." Tetrahedron 42.2 (1986): 655-661.

Mahmoud, Eyas, et al., "Renewable Production of Phthalic Anhydride from Biomass-Derived Furan and Maleic Anhydride," Green Chemistry 16, No. 1, pp. 167-175 (2014).

(Continued)

*Primary Examiner* — Michael Barker
*Assistant Examiner* — Jed A Kucharczk
(74) *Attorney, Agent, or Firm* — Hoffmann & Baron LLP

(57) ABSTRACT

The invention is directed to a process for the ring-opening of a cycloadduct obtainable from a reaction of a furanic compound and a diene, said process comprising contacting the cycloadduct with an acidic mixture comprising sulfuric acid and an activating agent to obtain a ring-opened product. The present invention is particularly directed a continuous process.

24 Claims, 3 Drawing Sheets

(56) References Cited

OTHER PUBLICATIONS

Figure 1:
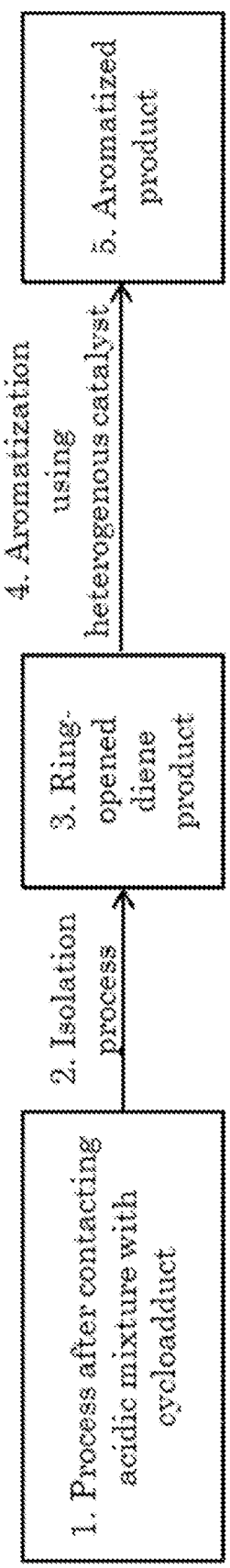

Newman, Melvin S., et al., "Improved Synthesis of 3-Methylphthalic Anhydride," The Journal of Organic Chemistry 42, No. 8, pp. 1478-1479 (1977).
Cava, M. P., et al., "2-Acetoxyfuran. A Study of its Preparation and its Behavior as a Diene," Journal of the American Chemical Society 78, No. 10, pp. 2303-2304 (1956).
International Search Report dated Sep. 6, 2019 for International Application No. PCT/NL2019/050250.

\* cited by examiner

DIELS-ALDER RING-OPENING PROCESS

The present invention relates to the preparation for ring-opening a cycloadduct comprising a 7-oxabicyclo[2.2.1]hept-2-ene core structure. In particular, the invention relates to a process to obtain such a ring-opened product by utilizing an acidic mixture.

Worldwide there is a growing consumption of aromatic molecules in fuels, plastics, coatings, textiles and many other applications. Said aromatic molecules are supplied from fossil fuels and security of feedstock supply has become much more important due to the recent developments in shale gas and increased fluctuations in oil price. Furthermore, there is a growing demand for sustainability, expressed in the use of renewable feedstock and the reduction of $CO_2$-footprint. As such, there is an increasing need for sustainable processes for the production of aromatic molecules (e.g. phthalic anhydride derivatives, benzenetricarboxylic acids etc.). Biomass, which is renewable and $CO_2$-neutral, appears to offer a good opportunity as an aromatic source.

Biomass consists of predominantly two components: lignin and (hemi-) cellulose. Both are polymeric macromolecules, where lignin consists of aromatic monomers and (hemi-)cellulose consists of C5 and C6 sugars. Superficially, lignin seems the most promising source for renewable aromatics, however, its depolymerization and the consequent selective isolation of aromatic monomers has proven to be cumbersome. In terms of selectivity, C5 and C6 sugars from (hemi-)cellulose, like glucose, xylose, mannose and arabinose, offer more potential as source for renewable aromatics. Said sugars can easily be converted to 2,5-di(hydroxymethyl)furfural, 5-(hydroxymethyl)furfural, 5-methoxymethylfurfural, 5-chloromethylfurfural, 2,5-dimethylfuran, furfural, furfuryl alcohol, 2-methylfuran or furan. Said compounds show promising opportunities for a sustainable process to synthesize aromatic compounds.

For instance, the furan core of the compounds mentioned in the paragraph above is able to react as a diene in a Diels-Alder reaction with dienophiles. The cycloadduct formed during said reaction can undergo a ring-opening and be carried on in further processing to yield aromatic products. Certain specific approaches for this are currently published for small scale, inefficient or expensive, batch experiments, which have limited potential to produce the millions of tons of aromatics required each year by industry.

For instance, Green Chemistry, 2014, 16, 167-175 describes the production of phthalic anhydride by reacting furan with maleic anhydride followed by a second reaction with mixed-sulfonic carboxylic anhydrides in excess methanesulfonic acid. A downside to the disclosed process is that methanesulfonic acid is used in a large access (10 molar equivalents), is expensive, and very difficult to recover and recycle, meaning that achieving significant production scale with this process is unlikely. Furthermore, the phthalic anhydride must be extracted with large volumes of toluene.

In WO 2010/012442 and Newman et al. JOC 42 (1977) 1478-1479, a ring-opening process for the preparation of 3-methylphthalic anhydride with sulfuric acid and sulfolane as co-solvent is reported. The conversion of the adduct of 2-acetoxyfuran and maleic anhydride into 3-acetoxyphthalic anhydride with acetic anhydride containing sulfuric acid is reported in Cava et al. JACS 78 (1956) 2303-2304.

Therefore, it remains of great interest to develop scalable technologies for the production process of renewable aromatics and an object of the present invention is to provide a process for the ring-opening of a cycloadduct comprising a 7-oxabicyclo[2.2.1]hept-2-ene core structure that does not suffer from one or more of the above-mentioned drawbacks.

Surprisingly, the inventors found a process that meets this objective by utilizing sulfuric acid in combination with an activating agent.

Accordingly, the present invention relates to a process for the ring-opening of a cycloadduct according to formula I

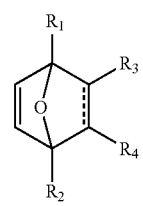

wherein $R_1$ and/or $R_2$ are independently selected from the group consisting of H, $C_1$-$C_{20}$ alkyl, CHO and hydrazones, oximes, hemiacetals and acetals thereof, $CH_2OH$ and esters and ethers thereof, $CO_2H$ and esters thereof, and amides and tertiary amines of $CH_2NH_2$, wherein the substituents $R_3$ and/or $R_4$ are independently selected from the group consisting of $CH_3$, acetals, hemiacetal, hydrazones and oximes of CHO, $CH_2OH$ and esters and ethers thereof, amides and tertiary amines of $CH_2NH_2$, and electron withdrawing groups H, $CF_3$, $CCl_3$, $CBr_3$, $Cl_3$, $NO_2$, CN, CHO, and $CO_2H$ and esters thereof, C(O)NQ, C(=NT)Q, $SO_2Q$, $SO_3Q$, COQ, COF, COCl, COBr, COI, wherein Q and T are independently H, or linear or branched $C_1$-$C_8$-alkyl, optionally substituted with halogens and optionally polymer supported, or a group such that $R_3$ and $R_4$ together represent —(CO)X(CO)—, wherein X=O, $CH_2$, NH, NMe, Net, NPr, NBu, NPh, or S and wherein said process comprises contacting the cycloadduct with an acidic mixture comprising sulfuric acid and an activating agent to obtain a ring-opened product. $R_2$ and $R_4$ may also together represent —$CH_2ZC(O)$—, wherein Z is selected from the group consisting of O, NH and S.

The solid-dashed bond ═══ in formula I represent a single or double bond. Preferably, the bond is a single bond, such that the cycloadduct is a compound according formula Ia:

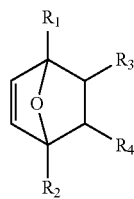

The presence of a single or double bond between the carbon atoms binding $R_3$ and $R_4$ typically depends on the starting materials in the preceding Diels-Alder reaction. In case the dienophile in this reaction comprised an alkene, said bond is typically a single bond while in case the dienophile in the reaction comprised an alkyne, said bond is typically a double bond.

In the context of the present invention the cycloadduct is typically derived from a Diels-Alder reaction of biomass derived furanics with a dienophile. A diene can contain a furanic core structure based on formula

and is typically substituted on the positioned herein numbered as 2, 3, 4, and/or 5 by one or more alkyl chains, heteroatoms and/or halogens. Said diene, when used in a Diels-Alder reaction, can provide a cycloadduct comprising a 7-oxabicyclo[2.2.1]hept-2-ene core structure based on the formula.

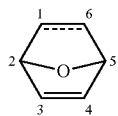

In the present invention, the cycloadduct undergoes a ring-opening at the bond between the bridged oxygen and the carbon at positions 2 and/or 5 when contacted with the acidic mixture.

In a preferred embodiment the sulfuric acid used in the acidic mixture comprises low amounts of water such as less than 3% based on the weight of sulfuric acid that is used in the method. Furthermore, it is preferred that the activating agent used in the acidic mixture reacts with the water that is present in the mixture to scavenge any present water.

The activating agent is typically selected from a group consisting of acylating agent, triflating agent, sulfonating agent, carbamylating agent, carbonylating agent. Preferably an acylating agent consisting of acetyl chloride, propionic anhydride, butyric anhydride, isobutyric anhydride, trimethylacetic anhydride, mixed anhydrides and combinations thereof is used. In said mixed anhydrides the groups adjacent to the acyl groups are different $C_1$-$C_{20}$ alkyl groups to one another. In a preferred embodiment of the present invention the acylating agent is acetic anhydride. These activating agents described are typically commercially available.

The bridging oxygen as shown in the above formula I will typically form a bond during the ring-opening process with a part of the activating agent. Without wishing to be bound to theory, the inventors believe that as such, the presence of the activating agent encourages fast ring-opening which limits the otherwise occurring unwanted retro-Diels-Alder reaction. The activating agent is therefore believed to contribute to the ring-opening at the bridged oxygen of the cycloadduct, such that said ring-opening is the main reaction.

By the above-described bond formation wherein a part of the activating group forms a bond with the bridging oxygen, another part of the activating group typically leaves the activating agent. Thus for instance, if the activating group comprises a symmetrical anhydride (i.e. a non-mixed anhydride), a corresponding acid with respect to the part of the activating agent that forms a bond with the bridging oxygen is also formed. More specifically, if the activating agent comprises the acetic acid anhydride, the oxygen is acylated and acetic acid is formed.

In case the activating agent comprises an anhydride, the activating agent can be represented by the chemical formula ActOAct such that a reaction of the activating group with the bridging oxygen results in ActOH and an Act-group that is attached to the ring-opened product. Thus, by a reaction of the activating agent with the cycloadduct, a reacted activating agent is formed, for instance said ActOH. Said reacted activating agent can typically also be formed by reaction with water, instead of the cycloadduct. In case of an incomplete reaction and/or an excess of activating agent with respect to the cycloadduct, unreacted activating agent may remain. In a preferred embodiment, the unreacted activating agent is removed under reduced pressure after ring-opened product is formed. This eliminates the requirement of an extraction step, as is the case in the prior art. Typically, the reacted activating agent has a lower boiling point than the unreacted activating agent (i.a. due to its smaller size) and is concomitantly removed. The unreacted activating agent can be recycled in the process for an increased overall efficiency.

In the present invention the activating agent is preferably mixed with sulfuric acid before contact with the cycloadduct. As is explained hereinabove, this typically results in an acidic mixture that is essentially free of water. In an embodiment the acidic mixture is typically at a temperature of 0 to 80° C. before contact with the cycloadduct. It is believed that a cooler acidic mixture, for instance a mixture below 10° C., the unwanted retro Diels-Alder reaction is hindered and competes less with the ring-opening process upon contact with the cycloadduct. In other words, the equilibrium of the Diels-Alder reaction may favor the Diels-Alder product and not the retro Diels-Alder product.

The cycloadduct undergoing the ring-opening in accordance with the present invention is preferably a compound according to formula I

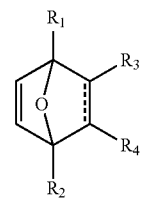

wherein $R_1$ and/or $R_2$ are independently selected from the group consisting of H, $C_1$-$C_{20}$ alkyl, CHO and hydrazones, oximes, hemiacetals and acetals thereof, $CH_2OH$ and esters and ethers thereof, $CO_2H$ and esters thereof, and amides and tertiary amines of $CH_2NH_2$. The substituents $R_3$ and/or $R_4$ are independently selected from the group consisting of $CH_3$, acetals, hemiacetal, hydrazones and oximes of CHO, $CH_2OH$ and esters and ethers thereof, amides and tertiary amines of $CH_2NH_2$, and electron withdrawing groups. The electron withdrawing group can be selected from the group consisting of H, $CF_3$, $CCl_3$, $CBr_3$, $CI_3$, $NO_2$, CN, C(O)Q, $CO_2Q$, C(O)NQ, C(=NT)Q, $SO_2Q$, $SO_3Q$, COQ, COF, COCl, COBr, COI, wherein Q and T are independently H, or linear or branched $C_1$-$C_8$-alkyl, optionally substituted with halogens and optionally polymer supported. $R_3$ and $R_4$ can also together represent —(CO)X(CO)—, wherein X=O, $CH_2$, NH, NMe, Net, NPr, NBu, NPh, or S. $R_2$ and $R_4$ may also together represent —$CH_2ZC(O)$—, wherein Z is selected from the group consisting of O, NH and S.

------ The solid-dashed bond in formula I represent a single or double bond. Preferably, the bond is a single bond, such that the cycloadduct is a compound according formula Ia:

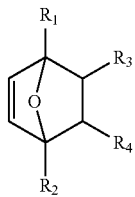

Ia

In the embodiments wherein $R_3$ and $R_4$ together represent —(CO)X(CO)—, wherein X=O, $CH_2$, NH, NMe, Net, NPr, NBu, NPh, or S, the cycloadduct has a structure according to formula Ib.

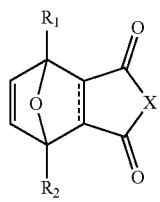

Ib

In the embodiments wherein $R_3$ and $R_4$ together represent —(CO)X(CO)—, the bond between the carbon atoms binding $R_3$ and $R_4$ is typically a single bond, in accordance with structure Ic.

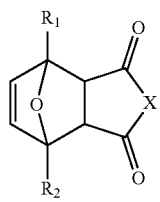

Ic

In the embodiments wherein $R_2$ and $R_4$ together represent —$CH_2ZC(O)$—, wherein Z is selected from the group consisting of O, NH and S, the cycloadduct has a structure according to formula Id.

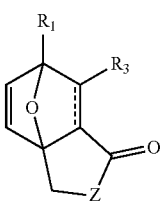

Id

In a preferred embodiment of the present invention, $R_1$ and $R_2$ both are H or methyl. In a further preferred embodiment, $R_1$ is hydrogen and $R_2$ is methyl.

As is described hereinabove, the cycloadduct typically is a product from a Diels-Alder reaction between a diene and a dienophile. The desired $R_1$ and $R_2$ substituents can be provided by selecting the appropriate diene. In the preferred embodiments described in the above paragraph, the dienes typically used in said Diel-Alder reaction can be furan, 2,5-dimethylfuran, 2-methylfuran and are typically derived from biomass.

Typically, a dienophile comprising at least one electron withdrawing group will facilitate the Diels-Alder reaction. In a preferred embodiment of the present $R_3$ and $R_4$ independently or together represent at least one electron withdrawing group.

In a preferred embodiment of the present invention, $R_3$ and $R_4$ together represent the electron withdrawing group —(CO)X(CO)—, wherein X=O, $CH_2$, NH, NMe, NEt, NPr, NBu, NPh, or S. More preferably $R_3$ and $R_4$ together represent —(CO)O(CO)—, —(CO)NMe(CO)—, —(CO)NEt(CO)— or —(CO)NPr(CO)—. As is described hereinabove, the cycloadduct typically derives from a Diels-Alder reaction between a diene and a dienophile. Thus, when $R_3$ and $R_4$ together represent —(CO)O(CO)—, the dienophile used in said Diels-Alder reaction to form the cycloadduct was maleic anhydride, whereas when $R_3$ and $R_4$ together represent respectively —(CO)NMe(CO)—, —(CO)NEt(CO)— or —(CO)NPr(CO)—, the dienophile used in said Diels-Alder reaction to form the cycloadduct were N-methylmaleimide, N-ethylmaleimide or N-propylmaleimide. These dienophiles are typically commercially available or can be obtained by the skilled person via well-known procedures.

Contacting the cycloadduct according to formula I with the acid mixture typically provides a ring-opened product. In said ring-opened product, the bond between the oxygen and at least one of the carbon atoms binding $R_1$ and $R_2$ is broken. comprising a ring-opened cyclohexene product according to formula II, an aromatized product according to formula III or a combination thereof,

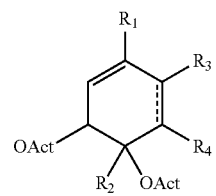

II

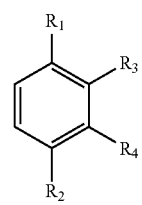

III wherein $R_1$, $R_2$, $R_3$ and $R_4$ as well as the solid-dashed bond are as defined for formula I.

In particular embodiments however, $R_1$, $R_2$, $R_3$ and $R_4$ may be different from those as defined in formula I. For instance, in case $R_1$, $R_2$, $R_3$ and $R_4$ comprise ester, anhydride, amide and/or imide groups at the like, at least partially, an in situ hydrolysis may occur due to water which may be added to or produced in the reaction mixture, leading to formation of a hydrolysate (i.e. a product of hydrolysis) such as carboxylic acid groups. Accordingly, for the ring-opened cyclohexene product according to formula II and/or the aromatized product according to formula III, $R_1$, $R_2$, $R_3$ and $R_4$ may be as defined for formula I and/or hydrolysates thereof. Depending on the completion of the hydrolysis, a mixture of products wherein $R_1$, $R_2$, $R_3$ and $R_4$ as defined for formula I and one or more hydrolysates thereof may be formed. For example, in embodiments wherein $R_3$ and $R_4$ in the cycloadduct together represent the electron withdrawing group —(CO)X(CO)—, this group may be hydrolyzed in situ such that $R_3$ and $R_4$ each represent —$CO_2H$ in formula II and/or III. Similarly, in the embodiments wherein $R_2$ and $R_4$ in the cycloadduct together represent —$CH_2ZC(O)$—, this group may be hydrolyzed in situ such that $R_2$ and $R_4$ in formula II and/or III represent —$CH_2Z$ and —$CO_2H$ respectively. The hydrolysates can be formed during contacting the cycloadduct with the acidic mixture and/or after this step, for instance just before or during isolation of the ring-opened product involving the addition of water (vide infra).

In the present invention the ring-opened cyclohexene product according to formula II wherein Act (herein also referred to as the activating group) is the above-described part of the activating agent that formed with the bridging oxygen.

The activating group (Act) in formula II is a remnant the activating agent.

Depending on the structure of the activating agent, OAct can represents an acylate, triflate, sulfonate, carbamylate, carbonylate, or combinations thereof. More specifically, Act can comprise structures such as —$SO_2CF_3$, —$SO_2Y$, —C(O)NYZ, —C(O)Y wherein Y and Z are independently H, linear or branched $C_1$-$C_{20}$-alkyl, phenyl or benzyl.

In the embodiments wherein the solid-dashed bond in formulae I and/or II ══════ represent a double bond, the aromatic product is typically a phenolic compound.

In a preferred embodiment of the present invention the activating group comprises —C(O)Y, wherein preferably Y=Me. This can be achieved by selected the activating agent comprising acetic acid anhydride.

It may be appreciated that the ring-opened cyclohexene product according to formula II may not be the only intermediate product towards the aromatized product according to formula III and that other ring-opened non-aromatic variations of the cyclohexene product may also be formed and isolated in accordance with the present invention.

The aromatized product of formula III is generally formed from the ring-opened cyclohexene product according to formula II by elimination of the —OAct group or groups as ActOH. In a typical embodiment of the invention, the eliminated reacted activating agent is a volatile compound such that it can be removed from the ring-opened product under reduced pressure. This may be carried out simultaneously with the removal of the unreacted activating agent.

In a particular embodiment of the present invention, the ring-opened cyclohexene product is isolated and then converted into the aromatized product. Said conversion preferably takes place by using a heterogeneous catalyst, wherein the heterogeneous catalyst facilitates the aromatization process by eliminating the —OAct group.

Contacting the cycloadduct with the acidic mixture can be carried out at a temperature ranging from −80 to 200° C., preferably in the range of −40 to 150° C., more preferably at in the range of −20 to 100° C., even more preferably 0 to 80° C. such as about 20° C. Said temperature is preferred to avoid the unwanted retro-Diels-Alder reaction, which was found to at least partially occur at higher temperatures.

In the present invention the cycloadduct can be contacted with the acidic mixture neat or dissolved in a suitable solvent, the former being preferred. A solvent can be suitably selected based on the specific cycloadduct used. In another, preferred embodiment of the present invention contact of the cycloadduct with the acidic mixture is achieved by slowly adding said cycloadduct neat to said acidic mixture. Said addition of the cycloadduct typically is preferably carried out in less than 1 hour, preferably less than 20 min, such as for instance about 15 minutes. The molar ratio of the activating agent to cycloadduct can typically be carried out within a range of 30:1 to 1:10, preferably in a range of 20:1 to 2:1. A preferred molar ratio of the present invention is less than 10:1. Whereas the molar ratio of sulfuric acid to cycloadduct is typically carried out in a range of 2:1 to 0.01:1, preferably in a range of 1:1 to 0.1:1. A preferred molar ratio of the present invention is about 0.5:1.

In a preferred embodiment of the present invention wherein acetic anhydride is used as the activating agent, the side-product formed during acylation comprises acetic acid.

A preferred embodiment of the present invention comprises heating. Heating the intermediate ring-opened cyclohexene product will allow conversion into aromatized product to proceed faster than at temperatures at or below 25° C. The heating can be carried out by inducing heat or passively heating the ring-opened cyclohexene product, for instance by allowing the product to warm up after it has been cooled. Heating of the ring-opened cyclohexene product to convert ring-opened cyclohexene product to aromatized product is typically carried out to a temperature in the range of 0 to 150° C., more preferably in a range of 15 to 100° C., most preferably in the range of 40 to 80° C. Said temperature is typically maintained at a maximum of 48 hours, more preferably for a maximum of 24 hours, even more preferably a maximum of 10 hours and even more preferably for a maximum of 6 hours. The time at which the temperature is maintained typically depends on the applied temperature. For instance, good results are obtained at maintaining a temperature of about 20° C. for 24 hours, 60° C. for 3 to 5 hours, and 80° C. for 45 to 90 minutes. It may even be possible to maintain a temperature of 100° C. for 30 minutes.

After formation of the ring-opened product is essentially complete, at least some, if not all of the remaining unreacted activating agent and/or reacted activating agent can be removed under reduced pressure. In a particular embodiment wherein the reaction mixture is heated by an external source, said mixture can be allowed to cool passively or by inducing cooling to an acceptable temperature such that the reaction mixture, when placed under a reduced pressure, allows evaporation of the volatile compounds in a controlled manner. Said removal under reduced pressure can be carried out at a pressure in the range of 0 to 1 bar, preferably in the range of 0.1 to 150 mbar, more preferably in the range of 1 to 100 mbar, even more preferably in the range of 5 to 50 mbar. Furthermore, the temperature of the reaction mixture is maintained during evaporation such that volatile compounds are removed, preferably at a range of 0 to 100° C. More preferable at a temperature in the range of 20 to 80° C. After an optional separation of the unreacted activating agent from the reacted activating agent, if required, the unreacted activating agent is preferably recycled in the process. This reduces the environmental footprint of the process, increases the sustainability and provides a more efficient and economically more advantageous overall ring-opening process. The separated reacted agent can be used in other processes, sold off, or dehydrated to re-form the activating agent and used again in the process.

In a typical embodiment of the present invention, isolation of the ring-opened product can be carried out by cooling the reduced reaction mixture to solidify the ring-opened product. Said cooling can be performed to a temperature in the range of −20 to 80° C., preferably 0 to 25° C. At the appropriate temperature and concentration, a seed may be added to induce crystallization.

The solidified ring-opened product is typically isolated from the reduced reaction mixture by filtering off said product.

In another embodiment of the present invention isolation of the ring-opened product can be carried out by the addition of an anti-solvent to the reduced reaction mixture. This can be carried out before or without first concentrating the reaction mixture. Said anti-solvent is preferably selected from an alcohol solvent, ether solvent, water or combinations thereof, preferably the anti-solvent is water. Typically, when an anti-solvent is added to the reduced reaction mixture, the ring-opened product solidifies resulting in a product herein referred to as the solidified ring-opened product. To achieve a desirable level of solidification at least 5 molar equivalents of anti-solvent with respect to the amount of the cycloadduct at the start of the reaction is typically added. Preferably a range of 5 to 50 molar equivalent anti-solvent is added to the reduced reaction mixture. These amounts are particular applicable to water as the anti-solvent.

Furthermore, higher levels of solidified ring-opened product can be achieved by cooling the reduced reaction mixture during and after addition of the anti-solvent. During addition and after addition—when water is used as the anti-solvent, said water may react with any residual anhydride and can cause a lot of heat to be released. This can lead to a mixture of products which is undesired for isolation purposes. Thus, cooling during and after the addition of water to the reduced reaction mixture may significantly slow down undesired reactions with water while said water still reacts with any residual anhydride. Cooling the reduced reaction mixture can be carried out at a temperature ranging from −20 to 25° C., preferably 0 to 10° C.

The solidified ring-opened product is typically isolated after the addition of the anti-solvent by filtering off said product.

The inventors find that it is preferred to remove the unreacted activating agent before the addition of water because of its reaction to give the reacted activating agent such as acetic acid. This reaction would prevent recycling of the unreacted agent such as acetic anhydride.

In yet another embodiment of the present invention, concentration of the reaction mixture under reduced pressure is not needed to isolate the ring-opened product. Such is the case when the ring-opened product solidifies in the reaction mixture either with or without inducing cooling. Then the solidified ring-opened product is isolated by filtration. To increase the yield, the product remaining in the filtrate can be isolated through cooling, anti-solvent, evaporative crystallization.

The invention can be described in a non-limited matter by the following particular embodiments.

In a first particular embodiment as illustrated in FIG. 1, ring-opened cyclohexene product is formed (1) and undergoes an isolation process (2) to give isolated ring-opened cyclohexene product (3). Elimination can be carried out using a heterogeneous catalyst, wherein the heterogeneous catalyst may form a heterogeneous solution with the solvent used in the elimination process or may act as the solvent itself (4) to give aromatized product (5).

Figure 2:
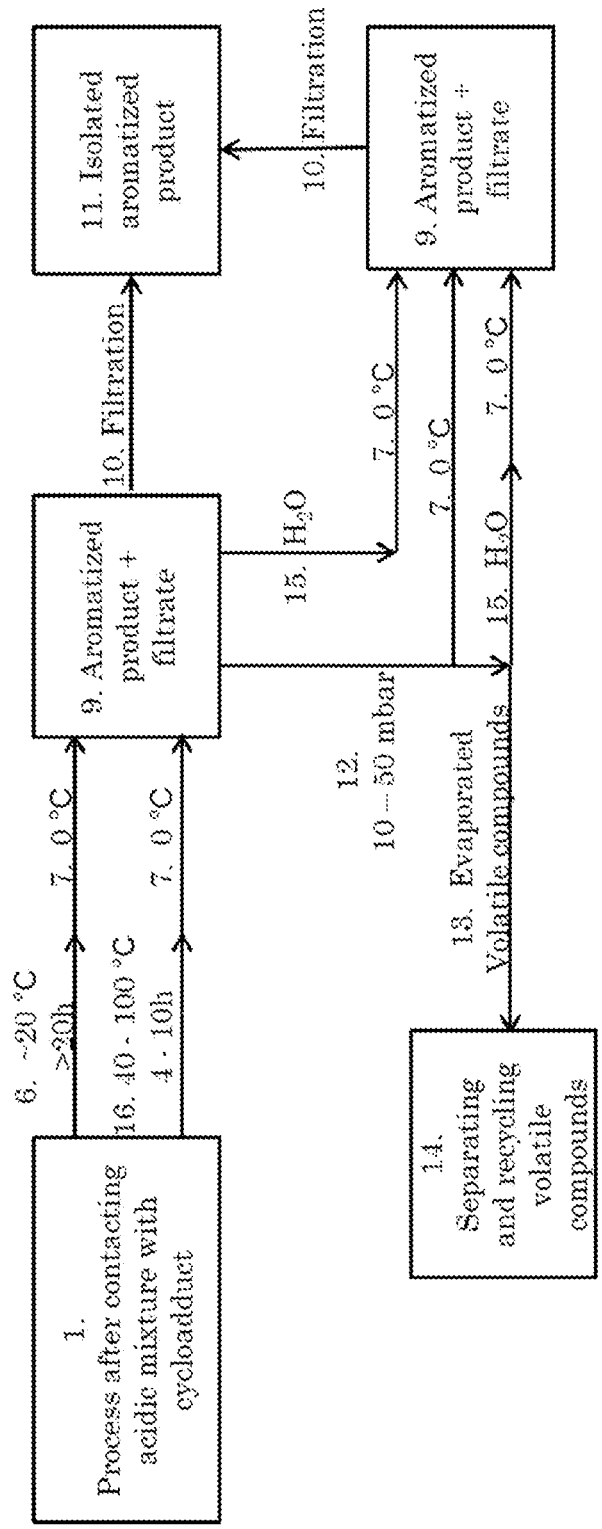

In a second particular embodiment as illustrated in FIG. 2, ring-opened cyclohexene product is formed (1) and maintained at a temperature at about 20° C. for more than 20 hours to convert said product to the aromatized product (6), then cooled to 0° C. (7) to solidify the aromatized product (9). The solidified aromatized product is filtered off (10) to be isolated (11) while the remaining compounds comprising unreacted reactants and products formed upon contact between cycloadduct and the acidic mixture remain in a filtrate.

It is possible in the above procedure that aromatized product which possibly remained in the filtrate can be recovered as follows. The volatile compounds in the filtrate can be evaporated under reduced pressure at a range of 5 to 50 mbar (12) to evaporate the volatile compounds (13). Said compounds can then be separated and recycled (14). Then 5 to 50 molar equivalents of water with respect to the amount of the cycloadduct is added (15), and optionally additionally cooled to about 0° C. (7), to solidify the remaining aromatized product out of the filtrate (9). A second filtration (10) will provide more isolated aromatized product (11).

It is also possible that the aromatized product solidifies after evaporation of the reduced pressure (12) and that no water needs to be added as is depicted in FIG. 2. Optionally, the filtrates after 9 can be fed back into the process (i.e. at 15).

Another possibility to recover more aromatized product from the filtrate as is depicted in FIG. 2 is by directly adding 15 to 50 molar equivalents of water with respect to the amount of the cycloadduct to the filtrate (15). This is then followed by cooling to 0° C. (7).

In a third particular embodiment according to FIG. 2, which differs from the above procedures above as follows, ring-opened cyclohexene product is formed (1) and maintained at a temperature in the range of 40 to 100° C. for 0.5 to 10 hours (16) to convert the ring-opened cyclohexene product to the aromatized product.

Figure 3:
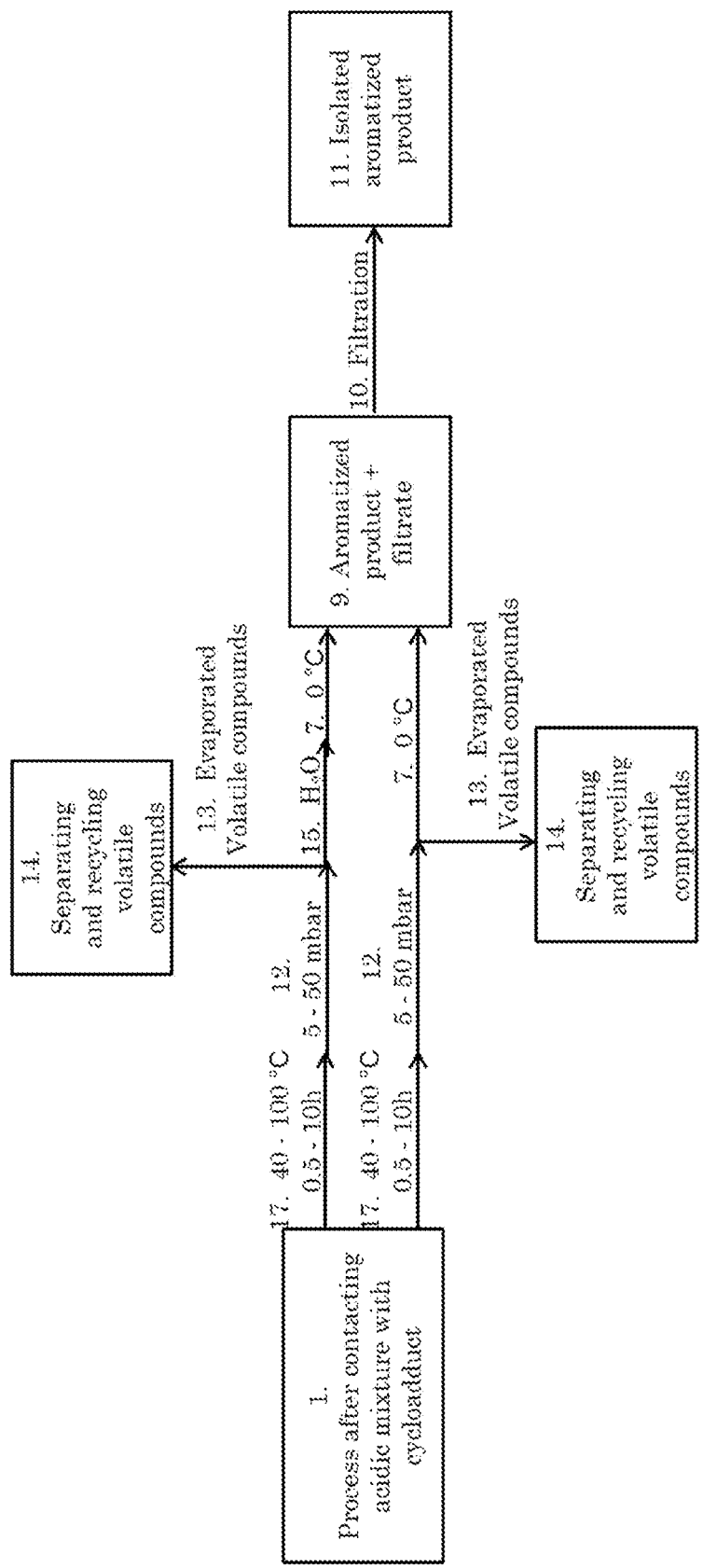

In a fourth particular embodiment, as illustrated in FIG. 3, ring-opened cyclohexene product is formed (1) and is maintained at a temperature in the range of 40 to 100° C. for 0.5 to 10 hours (17). The time can be reduced by addition of a catalyst such as a heterogeneous catalyst. Then under reduced pressure at a range of 5 to 50 mbar (12) the volatile compounds are evaporated (13). Said compounds can then be separated and recycled (14). 15 to 50 molar equivalents of water with respect to the amount of the cycloadduct is added to the reduced reaction mixture (15), cooled to 0° C. to solidify the aromatized product (9). The solidified aromatized product is filtered off (10) to be isolated (11).

In a fifth particular embodiment, as illustrated in FIG. 3, which differs from the fourth particular embodiment in that no water is added to the reduced reaction mixture as the product solidifies out by cooling the reaction mixture to 0° C.

In a sixth particular embodiment, as illustrated in FIG. 3 which differs from the fourth particular embodiment in that the temperature is maintained in the range of 40 to 100° C. for 0.5 to 10 hours (17) and the pressure is simultaneously reduced to a range of 5 to 50 mbar (12).

The present process is most preferably carried out as a continuous process. For instance, in a preferred embodiment, contacting the cycloadduct and the acidic mixture (e.g. at 5 to 35° C. for 15 to 60 minutes) leads to the ring-opened cyclohexene product according to formula II and a slurry or solution is obtained. The slurry or solution can then be heated (e.g. for 15 to 300 min at 20-100° C. or preferably 30 to 180 minutes at 60-90° C.) to form the aromatized product according to formula III, optionally catalyzed by a heterogeneous catalyst, followed by isolation of said aromatized product by evaporation crystallization, as described herein-above. The product obtained can then optionally further be purified by, for instance, re-dissolving and recrystallization from a solvent such as toluene. This overall process is very suitable for continuous operation.

Although isolation of the ring-opened product by extraction is possible, it is particularly preferred that the processes described herein are free of a solvent extraction step. This reduces cost and the environmental footprint of the process.

In a particular embodiment of the present invention, for instance wherein $R_3$ and $R_4$ of formula III together represent —(CO)O(CO)— or —(CO)NEt(CO)—, a hydrolysis can be carried out with the aromatized product according to formula III to obtain phthalic acid according to formula IV

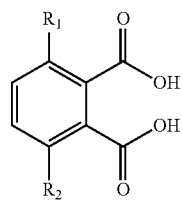

IV wherein $R_1$ and $R_2$ are described as hereinabove for formula III. Conventional methods can be used for said hydrolyzing process.

Compounds such as phthalic acid according to formula IV can also be obtained by hydrolysis taking place in situ (i.e. during the ring-opening and/or aromatization process), in particular when there is sufficient water in the reaction process available for this hydrolysis.

For the purpose of clarity and a concise description, features are described herein as part of the same or separate embodiments. However, it will be appreciated that the scope of the invention may include embodiments having combinations of all or some of the features describes.

The invention is further illustrated by the following examples.

EXAMPLE 1: PRODUCTION OF 3-MPA WITHOUT IN SITU EVAPORATION

A jacketed-reactor was cooled to −20° C. then acetic anhydride (12700 g) was added, with stirring. Sulfuric acid (1597 g) was then added slowly to limit the exotherm. When the internal temperature was <2° C., the solid Diels-Alder adduct of 2-methylfuran and maleic anhydride (5625 g) was added using a solid doser, maintaining an internal temperature of under 6° C. After complete addition, the mixture was warmed to 60° C., and held for 6 hours. The reaction mixture was then cooled to ~0° C. This caused a solid to precipitate. The solid was isolated by filtration and washed with ice-cold water (2000 ml) and dried in a vacuum oven (35° C., 2 mbar). Nuclear magnetic resonance (NMR) confirmed this product to be very clean 3-methylphthalic anhydride (2738 g, 54%). The filtrates were concentrated by vacuum distillation (50° C., ~20 mbar), then when no more distillate was observed, the concentrated mixture was stirred vigorously and cooled to 0° C., then ice-cold water (5600 g) was added. The mixture was again cooled to 0° C., then the formed solid was isolated by filtration, and washed with ice-cold water (1500 ml) and dried in a vacuum oven (35° C., 2 mbar). NMR confirmed this product to be quite clean 3-methylphthalic anhydride (3-MPA, 1268 g, 25%).

EXAMPLE 2: PRODUCTION OF 3-MPA WITH IN SITU EVAPORATION

To a reactor was charged acetic anhydride (420 ml) and this was cooled to around 0° C. with stirring, using an ice bath. Sulfuric acid (32 ml) was then added dropwise to limit the exotherm. This mixture was allowed to cool to ~1° C., then the solid Diels-Alder adduct of 2-methylfuran and maleic anhydride (200 g) was added portion-wise over a period or around 45 minutes, maintaining an internal temperature of under 6° C. After complete addition, the mixture was warmed to 50° C., and the reactor was set-up for vacuum distillation. Acetic acid and acetic anhydride (365 g total) were then removed by vacuum distillation at around 30 mbar. After around 4 hours, the reaction mixture was cooled to 0° C. with an ice/water bath, then ice-cold water (160 ml) was added dropwise, maintaining an internal temperature of less than 50° C. This yield a slurry, from which the solid was isolated by filtration, and washed with ice-cold water (200 ml) and dried in a vacuum oven (35° C., 2 mbar). NMR confirmed this product to be very clean 3-methylphthalic anhydride (129.4 g, 71.9%).

EXAMPLE 3: PREPARATION OF REACTION INTERMEDIATE 1

To a reactor was charged acetic anhydride (42 ml) and this was cooled to around 0° C. with stirring, using an ice bath. Sulfuric acid (3.08 ml) was then added dropwise to limit the exotherm. This mixture was allowed to cool to ~1° C., then the solid Diels-Alder adduct of 2-methylfuran and maleic anhydride (20 g) was added portionwise over a period or around 10 minutes, maintaining an internal temperature of under 15° C. The reaction was left to stand in an ice-bath for 60 minutes, during which time a solid precipitated. This was isolated by filtration and washed with ice-cold water (50 ml). NMR confirmed this product to be the corresponding ring-opened cyclohexene, a di-acetylintermediate (reaction intermediate 1).

EXAMPLE 4: CONVERSION OF REACTION INTERMEDIATE 1 TO 3-MPA

To a reactor was charged reaction intermediate 1 (100 mg), acetonitrile (1 ml) and silica (200 mg). This mixture was allowed to stir 1 hour at ambient temperature, then was analyzed by NMR. This showed almost complete conversion to 3-methylphthalic anhydride.

EXAMPLE 5: PURIFICATION OF 3-MPA WITHOUT ACTIVATED CARBON

To a reactor was charged crude 3-MPA (25 g—isolated from reaction mixture) and toluene (300 ml). The mixture was heated to reflux resulting in separation of a very small amount of brown oil. The light-colored solution was separated by decantation, and then cooled with stirring to induce crystallization. The formed solid was isolated by filtration and then washed with toluene (2×25 ml). This yielded a white solid (17.7 g, 71%). Concentration of the filtrates by rotary evaporation yielded a further white solid (5.8 g, 23%). NMR confirmed both isolated solids were confirmed to be highly pure 3-MPA.

EXAMPLE 6: PURIFICATION OF 3-MPA WITH ACTIVATED CARBON

To a reactor was charged crude 3-MPA (25 g—recovered from the reaction filtrates, and dark brown in color) and toluene (100 ml). The mixture was heated to reflux resulting in separation of the mixture into a biphasic system—predominantly a red colored solution, with a small amount of dark oil present. The red colored solution was separated by decantation and activated charcoal (4 g) was added. This was stirred at 100° C. for 30 minutes then filtrated while hot to remove the activated charcoal. The mixture was then cooled with stirring to induce crystallization. The formed solid was isolated by filtration and then washed with toluene (2×25 ml). This yielded a white solid (11.6 g, 46%). Concentration of the filtrates by rotary evaporation yielded a further white solid (7.3 g, 29%). NMR confirmed both isolated solids were confirmed to be highly pure 3-MPA.

EXAMPLE 7: CONTINUOUS PRODUCTION OF 3-MPA

A 8:1 molar mixture of acetic anhydride and concentrated sulfuric acid was prepared by adding sulfuric acid slowly to stirred acetic anhydride and cooling with an ice bath. This mixture was used as feed solution for the process. A continuously-stirred tank reactor (CSTR) was then heated to the desired temperature for contacting the cycloadduct (i.e. the Diels-Alder adduct) and acid mixture. A known volume of the acetic anhydride and concentrated sulfuric acid mixture was pumped into a CSTR reactor. The dosing of solid Diels-Alder adduct of 2-methylfuran and maleic anhydride from a solid-doser was then started at the desired rate. When the desired amount of solid Diels-Alder adduct had been added, the acetic anhydride and concentrated sulfuric acid pump was started at the desired rate. At the same time, a pump was started to pump the product mixture out of the CSTR at the desired rate, thus defining the residence time in the CSTR. The product mixture was pumped through a tubular reactor which was heated to the desired temperature, and had a length selected to determine the desired residence time. Samples from the CSTR and the tubular reactor were periodically taken to check progression and stability (by NMR, using an internal standard). In a specific example, a temperature of 25-30° C. was applied to the CSTR, and a residence time of around 20 minutes, resulting in no residual Diels-Alder adduct being present, and about 79% molar yield of reaction intermediate and ~19% molar yield of 3-methylphthalic anhydride exiting the CSTR (time-averaged over about 150 minutes). Passing this product solution through the tubular reactor at 60° C. for a residence time of around 24 minutes resulted in a product solution comprising about 54% molar yield of 3-methylphthalic anhydride.

EXAMPLE 8: RING-OPENING/AROMATIZATION WITH LESS H$_2$SO$_4$

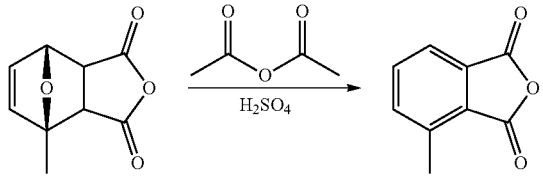

To a stirred flask containing acetic anhydride (113.4 g, 105 ml, 4 eq.) was added sulfuric acid (2.76 g, 1.5 ml, 0.1 eq.) and the mixture was cooled to ~0° C. (ice/water bath). To this was added 2-methylfuran:maleic anhydride Diels-Alder adduct (50 g) portion-wise over ~30 minutes. After complete addition, the mixture was heated to 50° C., held for 1 hour, and analyzed by NMR. Significant levels of the desired aromatic anhydride are present, but predominantly undesired retro-Diels-Alder has taken place, with >50 mol % maleic anhydride observed to be present.

EXAMPLE 9: RING-OPENING/AROMATIZATION WITH AQUEOUS WORK-UP

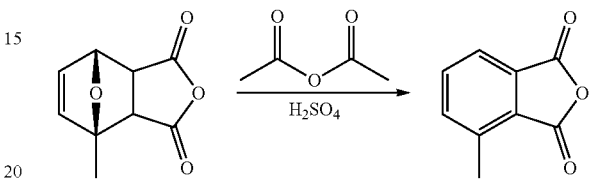

To a stirred flask containing acetic anhydride (113.4 g, 105 ml, 4 eq.) was added sulfuric acid (13.8 g, 7.5 ml, 0.52 eq.) and the mixture was cooled to ~0° C. (ice/water bath). To this was added 2-methylfuran:maleic anhydride Diels-Alder adduct (50 g) portion-wise over ~30 minutes. After complete addition, the mixture was heated to 50° C. and held for 4 hours. To the mixture was charged deionized water (25.0 g, 25.0 ml, 5 eq.) at a rate which maintained an internal temperature of <80° C., then the mixture was cooled to ~5° C. (ice/water bath). This caused a white solid to precipitate, and this was isolated by filtration and washed with ice-cold water (15 ml). The solid was dried in a vacuum oven (35° C., 10 mbar) to yield a white powder (28.11 g, 61.7%). Analysis by NMR confirmed the isolated product to be reasonably clean 3-methylphthalic anhydride. Analysis of the filtrate by NMR showed it to contain trace amounts of 3-methylphthalic acid.

EXAMPLE 10: RING-OPENING/AROMATIZATION TO MALEIMIDES

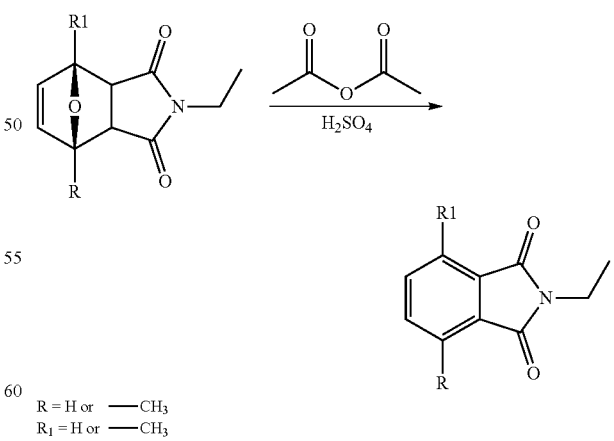

R = H or —CH$_3$
R$_1$ = H or —CH$_3$

To a stirred flask was charged acetic anhydride (422 mg, 391 μL, 4 eq.) followed by sulfuric acid (50.8 mg, 27.6 μL, 0.52 eq.) and the mixture was cooled to 0° C. (ice/water bath). To this was added N-ethyl-7-oxabicyclo[2.2.1]hept- 5-ene-2,3-dicarboximide (200 mg), portionwise over 10 minutes, maintaining a temperature below 10° C. and the mixtures was stirrer until the solids dissolved. The mixture was then heated to 60° C. and held for 2.5 hours, with the mixture being analyzed after 30, 60, 90 and 150 minutes by NMR. This shows a reasonably clean conversion, with around 20% N-ethylphthalimide having been formed after 150 minutes.

To a stirred flask was charged acetic anhydride (394 mg, 365 µL, 4 eq.) followed by sulfuric acid (47.5 mg, 25.8 µL, 0.52 eq.) and the mixture was cooled to 0° C. (ice/water bath). To this was added N-ethyl-4-methyl-7-oxabicyclo[2.2.1]hept-5-ene-2,3-dicarboximide (200 mg), portionwise over 10 minutes, maintaining a temperature below 10° C. and the mixtures was stirrer until the solids dissolved. The mixture was then heated to 60° C. and held for 2.5 hours with the mixture being analyzed after 30, 60, 90 and 150 minutes by NMR. This shows a reasonably clean conversion, with around 30% 3-methyl-N-ethylphthalimide having been formed after 30 minutes, and leading to more than 80% 3-methyl-N-ethylphthalimide after 150 minutes.

To a stirred flask was charged acetic anhydride (368 mg, 341 µL, 4 eq.) followed by sulfuric acid (44.2 mg, 24.0 µL, 0.52 eq.) and the mixture was cooled to 0° C. (ice/water bath). To this was added N-ethyl-4,6-dimethyl-7-oxabicyclo[2.2.1]hept-5-ene-2,3-dicarboximide (200 mg), portionwise over 10 minutes, maintaining a temperature below 10° C. and the mixtures was stirrer until the solids dissolved. The mixture was then heated to 60° C. and held for 2.5 hours with the mixture being analyzed after 30, 60, 90 and 150 minutes by NMR. This shows a reasonably clean conversion, with around 90% 3,6-dimethyl-N-ethylphthalimide having been formed after 60 minutes, and complete conversion to 3,6-dimethyl-N-ethylphthalimide after 150 minutes.

EXAMPLE 12: RING-OPENING/AROMATIZATION OF METHYL 7-OXABICYCLO[2.2.1]HEPT-5-ENE-2-CARBOXYLATE

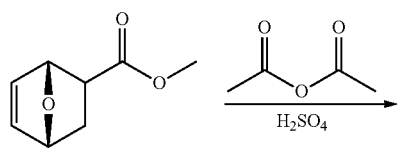

To a stirred reactor containing acetic anhydride (1229 mg, 1138 µL, 4 eq.), cooled to 0° C. (ice/water bath) was charged sulfolane (72.3 mg, 57.3 µL—internal analytical standard) and then sulfuric acid (148 mg, 80.2 µL, 0.5 eq.) and the mixture was stirred for 5 minutes at 0° C. Methyl 7-oxabicyclo[2.2.1]hept-5-ene-2-carboxylate (463.8 mg, 1 eq.) was added dropwise, maintaining a temperature below 10° C. Following complete addition, the mixture was stirred for 10 minutes at ~0° C., then heated to ~60° C. and held for a further 3 hours. The mixture was then analysed at various intervals by NMR. After 3 hours, 12% of the desired aromatic (methyl benzoate) has formed, with the rest of the mixture mainly ring-opened reaction intermediates.

EXAMPLE 13: RING-OPENING/AROMATIZATION OF DIMETHYL 7-OXABICYCLO[2.2.1]HEPTA-2,5-DIENE-2,3-DICARBOXYLATE

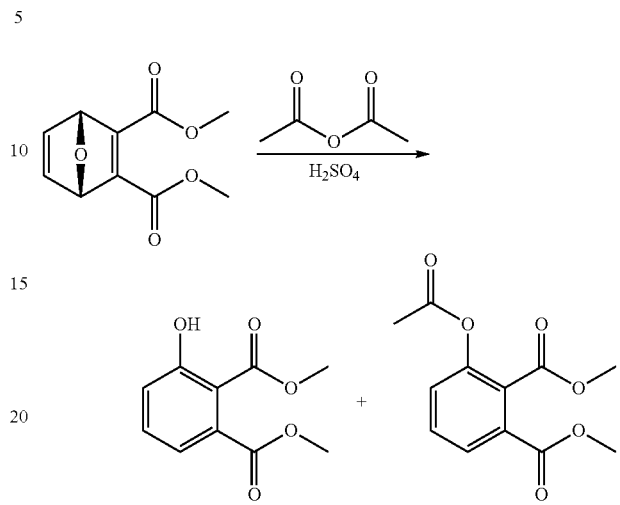

To a stirred reactor containing acetic anhydride (1229 mg, 1138 µL, 4 eq.), cooled to 0° C. (ice/water bath) was charged sulfolane (72.3 mg, 57.3 µL—internal analytical standard) and then sulfuric acid (148 mg, 80.2 µL, 0.5 eq.) and the mixture was stirred for 5 minutes at 0° C. Dimethyl 7-oxabicyclo[2.2.1]hepta-2,5-diene-2,3-dicarboxylate (632.1 mg, 1 eq.) was added dropwise, maintaining a temperature below 10° C. Following complete addition, the mixture was stirred for 10 minutes at ~0° C., then heated to ~60° C. and held for a further 3 hours. The mixture was then analyzed at various intervals by NMR. After 3 hours, a combined 32% yield of two aromatic products was observed (thought to correspond to dimethyl 3-hydroxyphthalate and dimethyl 3-acetoxyphthalate) in a ~1:1 ratio.

EXAMPLE 14: RING-OPENING/AROMATIZATION OF DIMETHYL 1,4-DIMETHYL-7-OXABICYCLO[2.2.1]HEPTA-2,5-DIENE-2,3-DICARBOXYLATE

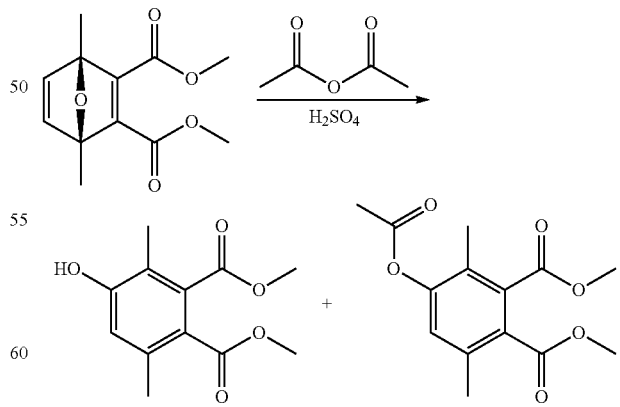

To a stirred reactor containing acetic anhydride (1229 mg, 1138 µL, 4 eq.), cooled to 0° C. (ice/water bath) was charged sulfolane (72.3 mg, 57.3 µL—internal analytical standard) and then sulfuric acid (148 mg, 80.2 µL, 0.5 eq.) and the mixture was stirred for 5 minutes at 0° C. Dimethyl 1,4-dimethyl-7-oxabicyclo[2.2.1]hepta-2,5-diene-2,3-dicarboxylate (716.5 mg, 1 eq.) was added dropwise, maintaining a temperature below 10° C. Following complete addition, the mixture was stirred for 10 minutes at ~0° C., then heated to ~60° C. and held for a further 3 hours. The mixture was then analyzed at various intervals by NMR. After 3 hours, a combined 83% yield of two aromatic products was observed, corresponding to dimethyl 4-hydroxy-3,6-dimethylphthalate and dimethyl 4-acetoxy-3,6-dimethylphthalate had formed in a ~3:1 ratio.

EXAMPLE 15: RING-OPENING/AROMATIZATION OF 7-OXABICYCLO[2.2.1]HEPT-5-ENE-2-CARBONITRILE

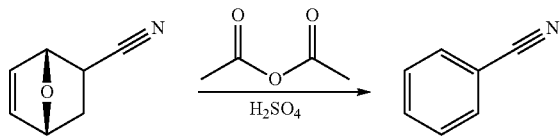

To a stirred reactor containing acetic anhydride (1229 mg, 1138 μL, 4 eq.), cooled to 0° C. (ice/water bath) was charged sulfolane (72.3 mg, 57.3 μL—internal analytical standard) and then sulfuric acid (148 mg, 80.2 μL, 0.5 eq.) and the mixture was stirred for 5 minutes at 0° C. 7-Oxabicyclo[2.2.1]hept-5-ene-2-carbonitrile (364.3 mg, 1 eq.) was added dropwise, maintaining a temperature below 10° C. Following complete addition, the mixture was stirred for 10 minutes at ~0° C., then heated to ~60° C. and held for a further 3 hours. The mixture was then analysed at various intervals by NMR. After 3 hours, a 51% yield of benzonitrile was observed, with the rest of the mixture mainly ring-opened reaction intermediates.

EXAMPLE 16: RING-OPENING/AROMATIZATION OF 1,4-DIMETHYL-7-OXABICYCLO[2.2.1]HEPT-5-ENE-2-CARBONITRILE

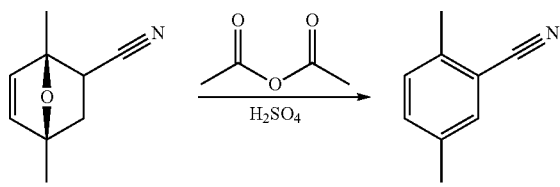

To a stirred reactor containing acetic anhydride (1229 mg, 1138 μL, 4 eq.), cooled to 0° C. (ice/water bath) was charged sulfolane (72.3 mg, 57.3 μL—internal analytical standard) and then sulfuric acid (148 mg, 80.2 μL, 0.5 eq.) and the mixture was stirred for 5 minutes at 0° C. 1,4-Dimethyl-7-oxabicyclo[2.2.1]hept-5-ene-2-carbonitrile (448.7 mg, 1 eq.) was added dropwise, maintaining a temperature below 10° C. Following complete addition, the mixture was stirred for 10 minutes at ~0° C., then heated to ~60° C. and held for a further 3 hours. The mixture was then analysed at various intervals by NMR. After 3 hours, a 5% yield of 2,5-dimethylbenzonitrile was observed, with the rest of the mixture mainly ring-opened reaction intermediates.

EXAMPLE 17: RING-OPENING/AROMATIZATION OF LACTONE DIELS-ALDER ADDUCT

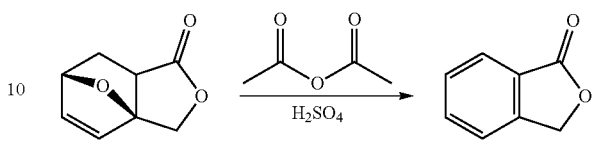

To a stirred flask containing acetic anhydride (300 mg, 277.8 μL, 4 eq.) was added sulfuric acid (36.0 mg, 19.6 μL, 0.5 eq.) and the mixture was cooled to ~0° C. (ice/water bath). To this was added 7,7a-Dihydro-3H-3a,6-epoxy-isobenzofuran-1(6H)-one (111.8 mg) portion-wise over ~15 minutes. After complete addition, the mixture was heated to 80° C. and held for 1 hour. The mixture was analyzed by NMR which showed a quantitative conversion to phthalide.

EXAMPLE 18: RING-OPENING/AROMATIZATION OF LACTONE DIELS-ALDER ADDUCT

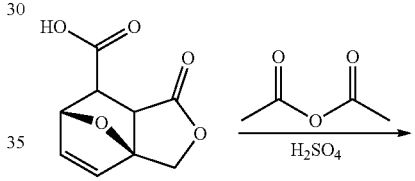

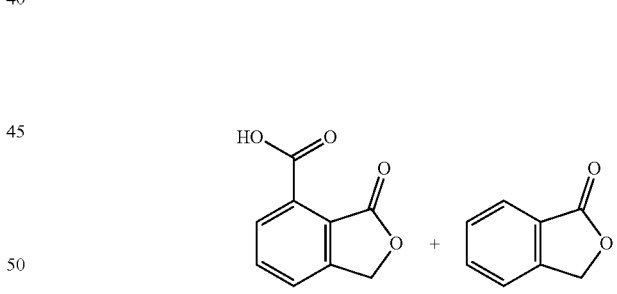

To a stirred flask containing acetic anhydride (38.49 g, 41.56 ml, 4 eq.) was added sulfuric acid (4.81 g, 2.61 ml, 0.52 eq.) and the mixture was cooled to ~0° C. (ice/water bath). To this was added 1,6,7,7a-tetrahydro-1-oxo-3H-3a,6-Epoxyisobenzofuran-7-carboxylic acid (20 g) portion-wise over ~60 minutes. After complete addition, the mixture was heated to 45° C. and held for 14 hours. The mixture was cooled to ~5° C. (ice/water bath) causing a solid to precipitate, and this was isolated by filtration. The solid was dried in a vacuum oven (35° C., 10 mbar) to yield a dark brown powder (10.18 g). Analysis by GCMS confirmed the isolated product to a ~1:3 ratio of the desired product 1,3-dihydro-3-oxo-4-isobenzofurancarboxylic acid:phthalide (produced by decarboxylation).

EXAMPLE 19: H$_2$SO$_4$AC$_2$O SYSTEM

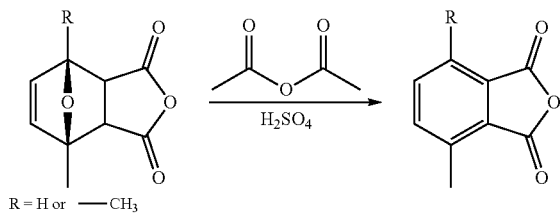

R = H or —CH$_3$

To a stirred reactor containing acetic anhydride (1229 mg, 1138 µL, 4 eq.), cooled to 0° C. (ice/water bath), was charged sulfolane (72.3 mg, 57.3 µL, 0.2 eq.—internal analytical standard) and then sulfuric acid (148 mg, 80.2 µL, 0.5 eq.) and the mixture was stirred for 5 minutes at 0° C. 1-methyl-7-oxabicyclo[2.2.1]hept-5-ene-2,3-dicarboxylic anhydride (542 mg, 1 eq.) was added portionwise, maintaining a temperature below 10° C. Following complete addition, the mixture was stirred for 20 minutes at ~0° C., then heated to ~60° C. and held for a further 4 hours. The mixture was then sampled while hot (to prevent crystallization) and analyzed by NMR. This showed the reaction to be incomplete, but a combined yield of 87% for the ring-opened reaction intermediate and 3-methylphthalic anhydride was observed.

EXAMPLE 20: H$_2$SO$_4$AC$_2$O SYSTEM

A process similar as described in Cava et al. JACS 78 (1956) 2303-2304 was carried out, albeit using methyl-7-oxabicyclo[2.2.1]hept-5-ene-2,3-dicarboxylic anhydride (i.e. a 2-methylfuran:maleic anhydride Diels-Alder adduct) as starting material. As from Cava et al., it is unclear exactly how the process was performed (either by adding the Diels-Alder adduct at high temperature, or by adding it at low temperature and then heating), two reactions were performed:
1) To a stirred flask containing acetic anhydride (21.6 g, 20 mL, 19 eq.) was added sulfuric acid (4 drops, ~90 mg, 0.08 eq.), and the mixture was heated to 120° C. To this was added 2-methylfuran:maleic anhydride Diels-Alder adduct (2 g) and the mixture was held at 120° C. for 1 hour, then analyzed by high performance liquid chromatography mass spectrometry (LCMS).
2) To a stirred flask containing acetic anhydride (21.6 g, 20 mL, 19 eq.) was added sulfuric acid (4 drops, ~90 mg, 0.08 eq.), and the mixture was cooled to ~0° C. (ice/water bath). To this was added 2-methylfuran: maleic anhydride Diels-Alder adduct (2 g) and when the solid had dissolved, the mixture was heated to 120° C., held for 1 hour and then analyzed by LCMS.

The same reaction was then performed using preferred conditions according to the present invention:
3) To a stirred flask containing acetic anhydride (21.6 g, 20 mL, 19 eq.) was added sulfuric acid (4 drops, ~90 mg, 0.08 eq.), and the mixture was heated to 120° C. To this was added 2-methylfuran:maleic anhydride Diels-Alder adduct (2 g) and the mixture was held at 60° C. for 1 hour, then analyzed by LCMS.

All reaction 1-3 proceeded to give the desired aromatic product, but the ratio of acetic anhydride:sulfuric acid gives rise to higher levels of undesired retro-Diels-Alder reaction (decomposition products). Adding the Diels-Alder adduct to the mixture at elevated temperature gives significantly poorer results than adding it at low temperature, and heating of the mixture at 120° C. gives rise to significant levels of (dark coloured) impurities (when compared to heating at ~60° C.).

COMPARATIVE EXAMPLE 1: H$_2$SO$_4$/SULFOLANE SYSTEM AT LOW TEMPERATURE

In a process similar to that described in Newman et al. JOC 42 (1977) 1478-1479, H$_2$SO$_4$ and sulfolane were used.

To a reactor containing concentrated sulfuric acid (42 ml), cooled to −55° C. (iso-propanol (IPA)/dry-ice bath) with stirring, was added sulfolane (17 ml). This caused the mixture to become quite viscous. 1-methyl-7-oxabicyclo [2.2.1]hept-5-ene-2,3-dicarboxylic anhydride (10 g, 1 eq.) was added at a rate such that the temperature did not exceed −45° C. Stirring at <−45° C. was labored due to the viscosity, but nearer to −45° C. the stirring was acceptable. After complete addition, the reaction was allowed to warm slowly to room temperature over ~3 hours, and then the mixture was poured into ice (167 g). This resulted in formation of a precipitate. When the ice had melted, the formed solid was isolated by filtration, washed with water and dried in a vacuum oven (35° C., 2 mbar) to yield a light yellow solid (3.2 g, 32%). This was analyzed by NMR and confirmed to be reasonably pure 3-methylphthalic acid. The remaining aqueous phase was extracted with EtOAc (2×50 ml) and the organic phase was washed with water, dried (Na$_2$SO$_4$), filtered and reduced to yield a dark brown oil which solidified partially on standing (2.5 g, 25%). This was analyzed by NMR and confirmed to be reasonably clean 3-methylphthalic acid with a small amount of 3-methylphthalic anhydride present.

COMPARATIVE EXAMPLE 2: H$_2$SO$_4$/SULFOLANE SYSTEM AT HIGHER TEMPERATURE

In a process similar to that described in Newman et al. JOC 42 (1977) 1478-1479, H$_2$SO$_4$ and sulfolane were used.

To a reactor containing concentrated sulfuric acid (42 ml), cooled to 5° C. (ice/water bath) with stirring, was added sulfolane (17 ml). 1-methyl-7-oxabicyclo[2.2.1]hept-5-ene-2,3-dicarboxylic anhydride (10 g, 1 eq.) was added at a rate such that the temperature did not exceed 7° C. After complete addition, the reaction was allowed to warm slowly to room temperature over ~2 hours, and then the mixture was poured into ice (167 g). This resulted in formation of a precipitate. When the ice had melted, the formed solid was isolated by filtration, washed with water and dried in a vacuum oven (35° C., 2 mbar) to yield a yellow solid (1.2 g, 12%). This was analyzed by NMR and confirmed to be impure 3-methylphthalic acid. The remaining aqueous phase was extracted with EtOAc (2×50 ml) and the organic phase was washed with water, dried (Na$_2$SO$_4$), filtered and reduced to yield a dark brown oil (1.4 g, 14%). This was analyzed by NMR and confirmed to be an impure mixture of 3-methylphthalic acid and 3-methylphthalic anhydride in a ~6:1 ratio.

The invention claimed is:

1. A process for the ring-opening of a cycloadduct comprising a cylcoadduct according to formula I,

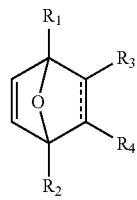

I wherein $R_1$ and/or $R_2$ are independently selected from the group consisting of H, $C_1$-$C_{20}$ alkyl, CHO and hydrazones, oximes, hemiacetals and acetals thereof, $CH_2OH$ and esters and ethers thereof, $CO_2H$ and esters thereof, and amides and tertiary amines of $CH_2NH_2$ and optionally polymer supported;

$R_3$ and/or $R_4$ are independently selected from the group consisting of $CH_3$, acetals, hemiacetal, hydrazones and oximes of CHO, $CH_2OH$ and esters and ethers thereof, $CO_2H$ and esters thereof, amides and tertiary amines of $CH_2NH_2$, and an electron withdrawing group that is selected from the group consisting of H, $CF_3$, $CCl_3$, $CBr_3$, $CI_3$, $NO_2$, CN, $SO_2Q$, $SO_3Q$, COQ, COF, COCl, COBr, COI, C(O)Q, $CO_2Q$, C(O)NQ, and C(=NT)Q, wherein Q and T are independently H, or linear or branched $C_1$-$C_8$-alkyl, optionally substituted with halogens and optionally polymer supported, or $R_3$ and $R_4$ together represent —(CO)X(CO)—, wherein X=O, $CH_2$, NH, NMe, NEt, NPr, NBu, NPh, or S;

or $R_2$ and $R_4$ together represent —$CH_2ZC(O)$—, wherein Z is selected from the group consisting of O, NH and S;

wherein ==== represent a single or double bond;

wherein said process comprises contacting the cycloadduct with an acidic mixture comprising sulfuric acid and an activating agent to obtain a ring-opened product; and wherein the molar ratio of sulfuric acid to cycloadduct is 2:1 to 0.01:1.

2. The process according to claim 1, wherein the activating agent is selected from the group consisting of an acylating agent, triflating agent, sulfonating agent, carbamylating agent, carbonylating agent, or combinations thereof.

3. The process according to claim 1, wherein the ring-opened product comprises a ring-opened cyclohexene product according to formula II, an aromatized product according to formula III or a combination thereof

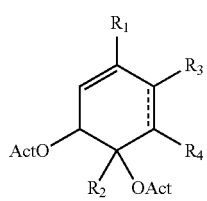

II

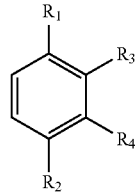

III wherein OAct represents —$OSO_2CF_3$, —$OSO_2Y$, —OC(O)NYZ, —OC(O)Y wherein Y and Z are independently H, linear or branched $C_1$-$C_{20}$-alkyl, phenyl or benzyl; and $R_1$-$R_4$ as well as the solid-dashed bond ==== are as defined for formula I and/or hydrolysates thereof.

4. The process according to claim 3, wherein the isolated ring-opened cyclohexene product according to formula II is brought into contact with a heterogeneous catalyst to give the aromatized product according to formula III.

5. The process according to claim 1, wherein the cycloadduct and the acidic mixture are contacted at a temperature in the range of −80 to 200° C.

6. The process according to claim 1, wherein said process is carried out with a molar ratio of the activating agent to cycloadduct in the range of 30:1 to 1:10.

7. The process according to claim 1, wherein said process comprises heating of the ring-opened product.

8. The process according to claim 7, wherein said heating is maintained for a maximum of 48 hours.

9. The process according to claim 1, wherein said process comprises removing at least part of the unreacted activating agent.

10. The process according to claim 9, wherein the removed unreacted activating agent is recycled into the process.

11. The process according to claim 1, wherein said process comprises isolation of the ring-opened product.

12. The process according to claim 1, wherein contacting the cycloadduct with an acidic mixture provides a slurry or solution comprising the ring-opened cyclohexene product according to formula II, wherein the slurry or solution is then heated to form the aromatized product according to formula III, optionally catalyzed by a heterogeneous catalyst, followed by isolation of said aromatized product by evaporative crystallization.

13. The process according to claim 12, wherein contacting the cycloadduct and the acidic mixture is carried out at 5 to 35° C. for 15 to 30 minutes and/or the slurry or solution is heated for 15 to 120 min at 20-100° C.

14. The process according to claim 1, wherein said process is a continuous process.

15. The process according to claim 1, wherein said process is free of a solvent extraction step.

16. The process according to claim 1, wherein said process further comprises the step of hydrolyzing the ring-opened product to obtain a phthalic acid.

17. The process according to claim 16, wherein the phthalic acid is according to formula IV, wherein $R_1$-$R_2$ are as defined for formula I

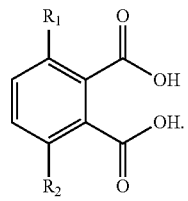

18. The process according to claim 1, wherein $R_1$ and $R_2$ both are hydrogen or methyl, or $R_1$ is hydrogen and $R_2$ is methyl.

19. The process according to claim 1, wherein $R_3$ and $R_4$ together represent —(CO)O(CO)—, —(CO)NMe(CO)—, —(CO)NEt(CO)— or —(CO)NPr(CO)—.

20. The process according to claim 1, wherein ═══ represents a single bond.

21. The process according to claim 2, wherein the activating agent comprises acetic anhydride.

22. The process according to claim 5, wherein the cycloadduct and the acidic mixture are contacted at a temperature in the range of 10 to 60° C.

23. The process according to claim 7, wherein the heating of the ring-opened product is done to a temperature in the range of 40 to 80° C.

24. The process according to claim 13, wherein the slurry or solution is heated for 30 to 90 minutes at 60-90° C.

* * * * *